United States Patent [19]

Podella

[11] Patent Number: 4,756,299

[45] Date of Patent: Jul. 12, 1988

[54] CHEMICAL HEATING PAD WITH DIFFERING AIR-ADMITTING PERFORATION SETS FOR DIFFERENT HEAT-GENERATION LEVELS

[75] Inventor: Carl W. Podella, Kenosha, Wis.

[73] Assignee: Hypertherm Technologies, Inc., Kenosha, Wis.

[21] Appl. No.: 121,929

[22] Filed: Nov. 18, 1987

Related U.S. Application Data

[63] Continuation-in-part of Ser. No. 941,335, Dec. 15, 1986, abandoned, which is a continuation-in-part of Ser. No. 909,987, Sep. 22, 1986, abandoned.

[51] Int. Cl.⁴ .............................. F24J 1/00; A61F 7/00
[52] U.S. Cl. .................................... 126/263; 126/204; 128/399; 128/403
[58] Field of Search .................. 126/263, 204; 44/3.1; 128/399, 402, 403

[56] References Cited

U.S. PATENT DOCUMENTS 1,620,581  3/1927  Smith ................................... 126/263
3,736,769  6/1973  Petersen ......................... 128/402 X Primary Examiner—Randall L. Green
Attorney, Agent, or Firm—Peter N. Jansson, Ltd.

[57] ABSTRACT

A heating pad of the type having a particulate chemical mixture, which is exothermically reactive in the presence of air, and a pair of opposed panels forming an envelope containing the mixture and admitting air to support the reaction. Differing perforation sets in the opposed panels allows the pad to generate two levels of heat and allows opposed body-contact surfaces of the pad to apply two different heat conditions to the human body.

19 Claims, 3 Drawing Sheets

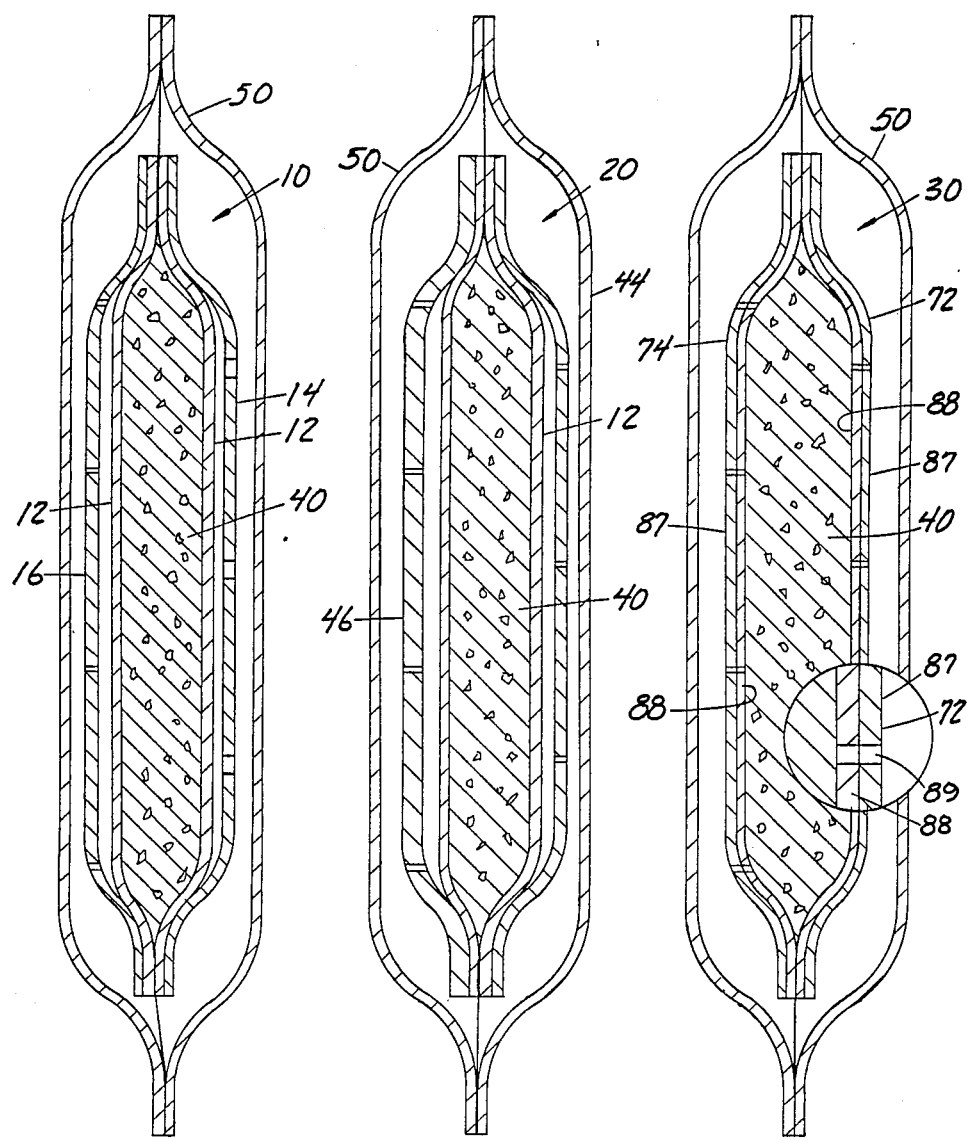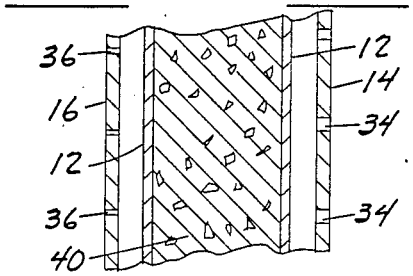

CHEMICAL HEATING PAD WITH DIFFERING AIR-ADMITTING PERFORATION SETS FOR DIFFERENT HEAT-GENERATION LEVELS

RELATED APPLICATIONS

This is a continuation-in-part of patent application Ser. No. 941,335, filed Dec. 15, 1986, now abandoned, which is a continuation-in-part of patent application Ser. No. 909,987, filed Sept. 22, 1986, now abandoned.

FIELD OF THE INVENTION

This invention is related generally to heating pads and, more particularly, to self-contained chemical heating pads for applying heat to the human body.

BACKGROUND OF THE INVENTION

Chemical heating pads of the type activated by exposure of a chemical mixture to atmospheric air reaching the mixture through openings in an envelope which contains the mixture are well known and have been known for many years.

Numerous patents have been granted for improvements in such chemical heating pads over the course of many decades, including the following U.S. patents: U.S. Pat. Nos. 1,434,576 (Wertheimer); 1,609,958 (Perrault); 1,620,581 (Smith); 3,301,250 (Glasser); 3,976,049 (Yamashita et al.); 4,106,478 (Higashijima); 4,282,005 (Sato et al.); 4,366,804 (Abe); 4,516,564 (Koiso et al.); and 4,573,447 (Thrash et al.).

A typical example is U.S. Pat. No. 3,976,049, which discloses a warming pad having an exothermic composition including iron powder, a chloride or sulfate salt, carbon powder, and water in a two-layered bag made of an air-permeable cloth layer inside a film layer with aeration holes. The entire pad is contained in an impermeable envelope which is opened to allow removal of the pad. This allows atmospheric air to pass through the aeration holes and permeable layer of the bag, which exposes the composition to air (specifically its oxygen) to begin the exothermic reaction. This device is typical of such heating pads.

While there have been many developments in the field of chemical heating pads, there remain significant problems and shortcomings with heating pads of this general type. For example, such pads are often too hot or not hot enough for the intended purpose.

It is known that the amount of heat produced, the rate of heat generation, and achievable temperatures are dependent on, inter alia, the chemical composition of the mixture inside the pad, the size and number of holes in the pad exposed to the atmosphere, and the thickness of the material of the pad. These factors often have been considered in the prior art in seeking to provide chemical heating pads meeting particular requirements.

One object of some developments of the prior art has been to achieve constant and predictable heat conditions on the major surfaces of an air-dependent chemical heating pad. In certain other cases the object has been to have heat emitted from only one side of such a heating pad, with the second side shielded or insulated to prevent heat emission. These objects contrast sharply with a principal object of this invention, that is, to achieve different heat-generation levels and different useful heat conditions when opposite sides of a pad are applied to the body or other surface to be heated.

When chemical heating pads are used on human skin for various purposes, they are frequently either too hot or not hot enough for the skin of the users. That sensitivities to topically-applied heat vary greatly in this way is established. It is also known, in the field of therapeutic heat treatment, that heat sensitivity varies not only from person to person but according to the location on the body of the person being treated. For any person, some areas of skin are better able to receive applications of heat.

The inability of prior air-dependent chemical heating pads to adequately satisfy varying sensitivities of users is well known, and has limited the use of such heating pads. Pads with only a single level of heat generation and heat transfer or only one heat-transfer surface are simply not suitable for therapeutic use unless special accommodations are made. There is a long-standing and clear need for an improved self-contained heating pad.

OBJECTS OF THE INVENTION

It is an object of this invention to provide an improved chemical heating pad overcoming some of the problems and shortcomings of heating pads of the prior art.

Another object of this invention is to provide an improved self-contained chemical heating pad which may be used by people with widely varying sensitivities to heat applied to the skin.

Another object of this invention is to provide an improved chemical heating pad of the air-dependent type having two heat-generation levels.

Another object of this invention is to provide an improved chemical heating pad with significantly different but useful heat conditions on its opposite surfaces as each is applied against the body of a user.

These and other important objects will be apparent from the descriptions which follow.

SUMMARY OF THE INVENTION

This invention is an improved chemical heating pad of the air-dependent type, which overcomes certain problems and shortcomings of prior art devices, including those mentioned above. The heating pad of this invention is of the type having a particulate chemical mixture which is exothermically reactive in the presence of air and first and second opposed panels forming an envelope which contains the mixture while admitting air.

In the heating pad of this invention, the first panel has a first body-contact surface (its outer surface) and a first set of air-admitting perforations which extend from the first body-contact surface to inside the envelope. The second panel has a second body-contact surface (its outer surface) and a second set of air-admitting perforations which extend from the second body-contact surface to inside the envelope. The second set of perforations differs from the first set of perforations, such that two different heat conditions develop and may be applied to the human body by the two body-contact surfaces.

With the first body-contact surface applied to the skin, the second set of perforations, which begin on the second body-contact surface, are available to admit air to the contained reactive mixture in a particular way, and as a result a particular heat generation occurs within the pad and is applied to the skin through the first body-contact surface.

Likewise, with the second body-contact surface applied to the skin, the first set of perforations, which begin on the first body-contact surface, are available to admit air to the contained reactive mixture in a different way, with the result that a different level of heat generation occurs within the pad and is applied to the skin through the second body-contact surface.

In each case, the set of perforations of the panel opposite the panel which is in contact with the skin play an important role in determining the level of the temperatures applied and the amount of heat transfer occurring.

In highly preferred embodiments, each of the first and second panels, except for the perforations, is substantially air- and moisture-impermeable. The perforations are made in air- and moisture-impermeable material. The panels, at least one and preferably both of them, are laminates, including at least one layer of the air- and moisture-impermeable material, as already described. Such laminate preferably also includes a layer of air- and moisture-permeable material. Such air- and moisture-permeable material is preferably an outer layer to form one of the body-contact surfaces, giving it an excellent tactile quality.

In preferred embodiments, the chemical mixture is preferably a moist particulate mixture of carbon powder, iron powder, vermiculite, and a salt-water solution which is selected and included in amounts appropriate to provide an exothermic reaction in air.

Some preferred heating pads in accordance with this invention have their chemical mixtures, their first and second panels, and their differing perforation sets selected to provide temperatures, on the surfaces to be applied to the body, within a range of about 57.5–65 degrees C. at the first body-contact surface and within a range of about 50–57.5 degrees C. at the second body-contact surface. This invention is readily capable of providing controlled heat to meet these preferred temperature range requirements.

The differing sets of air-admitting perforations allow the differing heat-generation and heat-transfer characteristics which are at the heart of this invention. Such differing perforation sets can differ in various ways, in size, number, shape, arrangement, length, and/or other ways, in each case allowing a predetermined extent and/or character of air admission to achieve the desired different heat characteristics.

In one preferred structure of this invention, the perforations of the first set are of greater size than the perforations of the second set. This allows greater air flow through the first panel than through the second panel, which contributes to the different heat conditions.

In another preferred structure, the first set of perforations has a greater number of perforations than the second set of perforations. This allows better access of air to the chemical mixture, thereby contributing to the different heat conditions and doing so independently of the relative extent of air flow by means of the second set of perforations.

In certain preferred embodiments of this invention, the first and second panels may differ in thickness. This can contribute to the different heat conditions.

The objects of this invention are achieved by the heating pad as described above. The heating pad of this invention provides a predetermined and controlled higher level of intensity of heat at one body-contact surface of the heating pad and a predetermined and controlled lower level of heat at the other body-contact surface.

The heating pad of this invention, prior to use, is kept in an air- and moisture-impermeable envelope. When it is time for use, the pad is removed from such air- and moisture-impermeable envelope. To initiate the exothermic reaction quickly, the pad is shaken or massaged once or twice. During its use, the amount of both heat generation and heat transfer will depend on which body-contact surface is applied to the skin. In large measure, the amount of both heat generation and heat transfer will depend on which body-contact surface is not applied to the skin, so that it is exposed to the atmosphere.

A person to whose body the pad will be applied, whether a hospital patient, athlete, or other individual requiring heat, can select the side of the heating pad for application to the skin or body member to be treated according to the individual comfort level. The choice may be made by a nurse or other medical personnel treating the person, with or without consultation, depending on the therapeutic requirements.

For a practical therapeutic pad in accordance with this invention, it has been found that the body-contact surface with a greater heat transfer heat should be at a temperature of from about 57.5–65 degrees C. for contact with the body, while the other body-contact surface with a lower heat transfer should be maintained at a temperature of from about 50–57.5 degrees C. for contact with the body. This allows a skin temperature of from about 40–45 degrees C. to be attained regardless of which side of the heating pad is used. The choice of which side to apply to the skin of a particular patient will depend on whether his or her tolerance level is good because of good circulation and/or limited fatty tissue, or poor because of poor circulation and/or excess fatty tissue.

It will be understood that heat levels can be controlled within relatively narrow ranges by proper selection of the chemical composition to be placed in the envelope, by the number and size of the perforations in the first and second panels, and by proper selection of materials. In selecting materials and perforation characteristics, use can be made of instruments such as a Gurley air flow tester, and/or empirical results may be collected by making pads and adjusting pad characteristics.

The devices of the present invention, therefore, are well adapted for therapeutic heat application to patients. The different levels of heat at the opposed body-contact surfaces can accommodate either the individual sensitivity of a person to heat, or the sensitivity of a particular part of his or her body.

BRIEF DESCRIPTION OF THE DRAWINGS

FIG. 3 is a sectional view of the heating pad of FIG. 1 taken along section 3—3, as indicated in FIG. 1, in a gas- and moisture-impermeable container.

FIG. 4 is an enlarged fragmentary view of FIG. 3.

FIG. 7 is a sectional view of the heating pad of FIG. 5 taken along section 7—7, as indicated in FIG. 5, again in a gas- and moisture-impermeable container.

FIG. 8 is a partially-magnified sectional view of another heating pad, a highly preferred embodiment of this invention, again in a gas- and moisture-impermeable container.

DETAILED DESCRIPTIONS OF PREFERRED EMBODIMENTS

Figure 5:
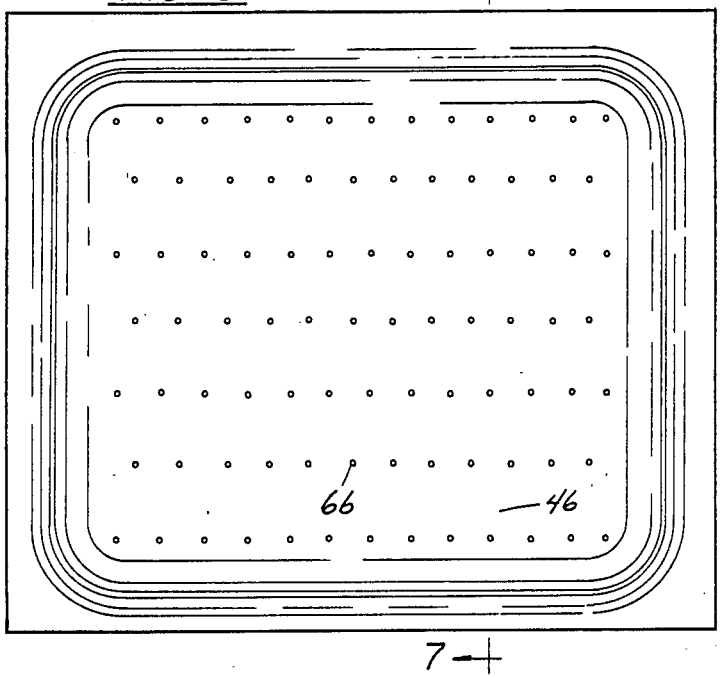
FIG. 5 is a front elevation of another heating pad in accordance with this invention.
Figure 6:
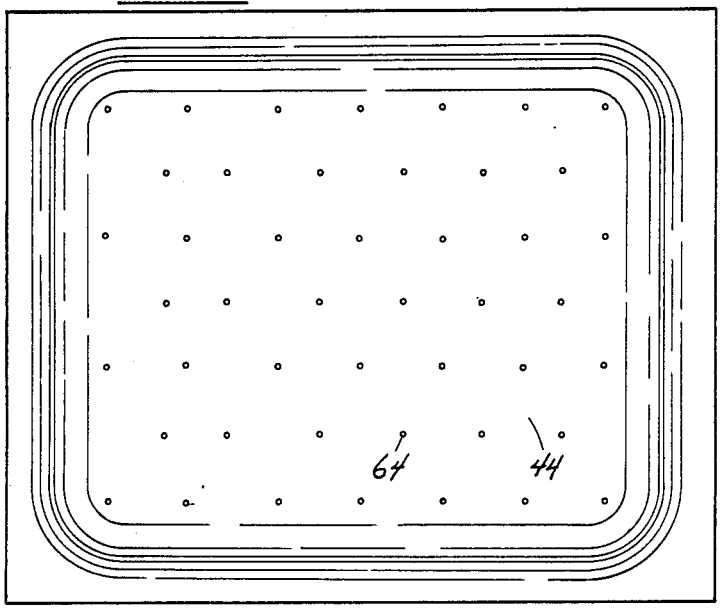
FIG. 6 is a rear elevation of FIG. 5.

Three embodiments of the invention are shown in the drawings, including a heating pad 10 in FIGS. 1-4, a heating pad 20 in FIGS. 5-7, and a heating pad 30 in FIG. 8. Throughout the drawings, like numbers are used to identify similar elements.

Heating pad 10 shown in FIGS. 1-4, as shown in FIGS. 3 and 4, includes a chemical mixture 40 contained within an envelope. The envelope has first and second opposed panels 22 and 24 forming the containment space for chemical mixture 40. Opposed panels 22 and 24 each have two separate layers, inner layers formed by bag 12 and outer layers 14 and 16.

The inner layer in each case is part of a bag 12 made of an air- and moisture-permeable material such as a non-woven or woven cloth. One preferred material is a polyester non-woven material. The material of bag 12, while in itself capable of passing air at a high rate, contains particulate chemical mixture 40 very well.

Bag 12 is between outer layers 14 and 16. Outer layers 14 and 16 are formed of sheets of a material which, apart from the perforations extending through them, are gas- and moisture-impermeable. Outer layers 14 and 16 each provide a body-contact surface. When one body-contact surface is against the body, the other is exposed to the atmosphere such that air can pass therethrough.

The entire heating pad 10 is stored until time of use in a gas and moisture-impermeable container 50, which is illustrated in FIG. 3.

Figure 1:
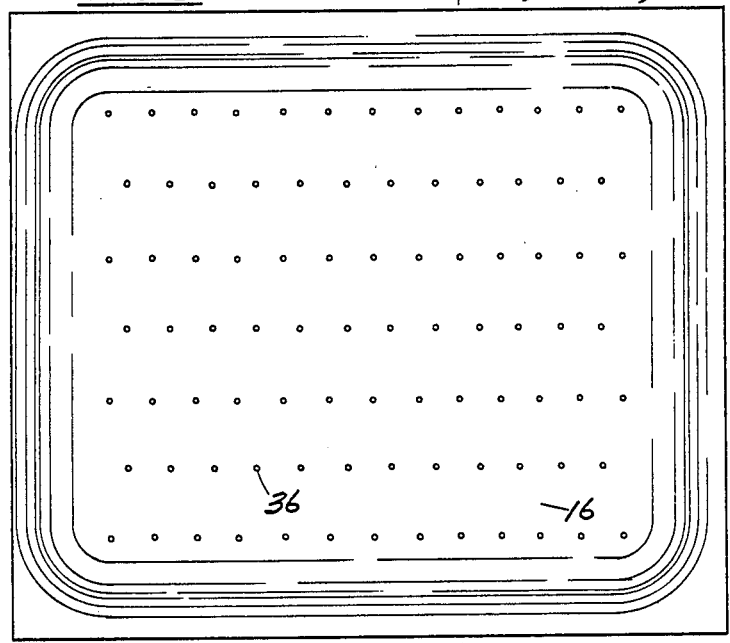
FIG. 1 is a front elevation of a heating pad in accordance with this invention.
Figure 2:
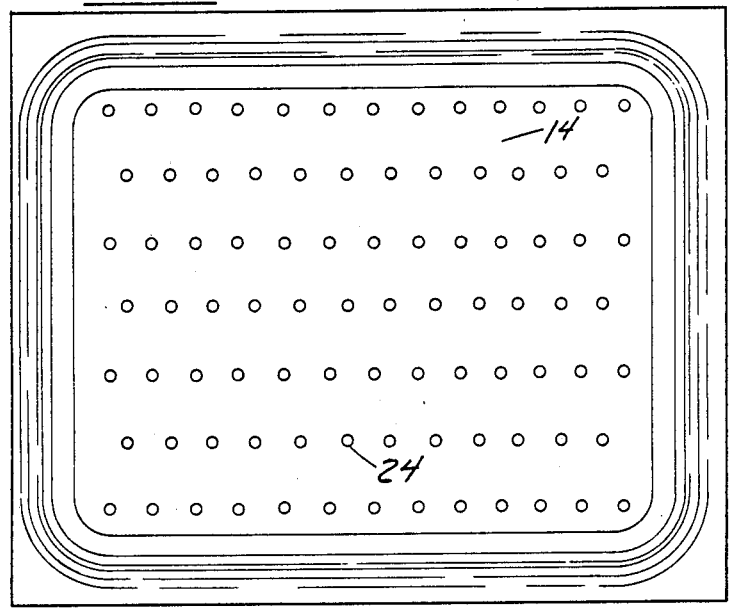
FIG. 2 is a rear elevation of FIG. 1.

As illustrated best in FIGS. 1, 2 and 4, outer layers 14 and 16 contain different sets of air-admitting perforations. While outer layers have about the same number of perforations, outer layer 14 has perforations 34 which are larger than the perforations 36 which are in outer layer 16. Thus, the admission of air to the chemical mixture 40 is faster through panel 22 than it is through panel 24. Thus, when outer layer 16 is against the human body, the exothermic reaction is faster and hotter, thereby producing a higher level or intensity of heat than when heating pad 10 is used by applying outer layer 14 to the body.

Heating pad 20, shown in FIGS. 5-7, is generally similar to heating pad 10. However, heating pad 20 has outer layers 44 and 46 which differ from outer layers 14 and 16 of heating pad 10. FIGS. 5 and 6 illustrate that the sets of perforations in outer layers 44 and 46 differ. While each perforation 64 in outer layer 44 is similar in size to perforations 66 in outer layer 46, there are twice as many in outer sheet 46 as in outer sheet 44. Thus, when outer layer 44 is applied to the body, air reaches more portions of chemical mixture 40 more easily. Even if perforations 64 were enough larger than perforations 44 to allow the same rate of air passage through both sides of the pad, the better distribution of air to the reactive mixture would provide more intense heat generation.

Outer layer 46 is substantially thicker than outer layer 44. This contributes to the different heat conditions available through selective contact with the opposite panels of heating pad 10. Such difference in panel thickness has the effect as well of changing the characteristics of the air-admitting perforations extending therethrough. In one preferred embodiment, the thickness of outer layer 44 is about 0.007 inch while the thickness of outer layer 46 is 0.013 inch.

Heating pad 30, shown in FIG. 8, is a highly preferred embodiment of this invention having first and second panels 72 and 74 which are laminates; that is, each panel 72 and 74 has two inner and outer layers which are adhered together all across their common surfaces. Each laminate is a composite of a non-woven polyester cloth outer layer 87 and a polyethylene film inner layer 88.

As shown in the magnified portion of FIG. 8, in heating pad 30 perforations 89 extend straight through both layers 87 and 88, unlike the air-admitting perforations (or passages) of heating pads 10 and 20 which include the perforations in the outer layers and the interstices of the inner bag. Perforations 89 in panel 72 are of one size and/or pattern, while the perforations (not shown) in panel 72 are or another size and or pattern. Such differing sets of perforations provide the desired different heat intensities and heat transfer characteristics.

As with heating pads 10 and 20, heating pad 30 is stored until time of use in a gas and moisture-impermeable container 50.

The chemical mixture in the heating pads shown in the drawings include an intermediate having 30% by weight of vermiculite, 55% by weight of a 10% sodium chloride solution in water, and 15% by weight of carbon having of fine particle size, such intermediate combined on a 50/50 weight ratio with iron powder of fine particle size.

The embodiments of FIGS. 1-7 may be made by carrying out the following steps in sequence:

1. A 10% sodium chloride solution is prepared by mixing sodium chloride in tap water or deionized water until it is dissolved.

2. The sodium chloride solution is added to a vessel containing the vermiculite with gentle stirring action to achieve uniformity without crushing the vermiculite.

3. The carbon is added to the vermiculite/sodium chloride solution mixture and blended to uniformity, thus completing preparation of the intermediate.

4. Bag 12 is prepared by heat-sealing an air- and moisture-permeable non-woven cloth laminate on three edges to form a pouch.

5. The intermediate is loaded into the pouch.

6. The iron powder is then loaded into the pouch which already contains the intermediate.

7. The fourth edge of the pouch is then heat sealed and the sealed pouch is then shaken to obtain uniformity of the chemical mixture.

8. Air- and moisture-impermeable materials are selected or formed, having the desired thicknesses and having perforations (formed by punching, laser cutting, or mechanical cutting) as desired. The previously-sealed pouch is then sandwiched between layers of such differing air- and moisture-impermeable materials, which are then heat-sealed along their common edges.

9. The heating pad is then placed into an air- and moisture-impermeable bag which is heat-sealed along its common edges, sealing it such that the chemical mixture will not react until desired.

In the embodiment of FIG. 8, the chemical mixture is added directly to an envelope prepared from the laminates, having layers and perforations as described above, and the envelope then sealed. The heating pad is then packaged as described in step 9 above.

The heating pads in accordance with this invention may be made using a variety of other production methods. Acceptable method would be apparent to those skilled in the art who are familiar with this invention.

The chemical mixture may be varied in a number of ways.

Iron powder is preferred because it reacts readily with atmospheric oxygen in the presence of moisture to generate heat. And, because it is dense it is a good thermal conductor. The fineness of the powder can be varied to change the rate of the reaction. Other reactive metal powders, such as magnesium, zinc, and aluminum, can be utilized.

The carbon powder of the reaction mixture is useful because of its large surface area to weight ratio. The carbon contains a network of holes and channels, enabling the carbon to absorb atmospheric oxygen in large amounts to supply the oxygen for the oxidation reaction. The oxygen-absorbing capacity is greatly increased when the carbon is slightly wet, as it is when mixed with the sodium chloride solution. The carbon powder, however, can be replaced by other particulate materials such as talc.

Sodium chloride is utilized in order to catalyze the oxidation of iron. It is particularly desirable in that it is readily available, inexpensive, and the toxicity is low. The sodium chloride, however, can be replaced by other suitable chlorides and sulfates, such as ferric sulfate, potassium sulfate, sodium sulfate, and magnesium sulfate, potassium chloride, calcium chloride, and magnesium chloride.

Additionally, the ratios of the components of the chemical mixture can be varied substantially in order to make either a hotter or cooler reaction mixture. It is understood that, as a general rule, the greater the amount of metal powder the hotter the reaction. All of these characteristics are known to those skilled in the art.

Formula modifications will generally be within the following parameters: sodium chloride in an amount of about 0.5-30 parts by weight per 100 parts of iron powder; carbon in an amount of about 2.5-400 parts by weight per 100 parts of iron powder; and water in an amount of about 10-250 parts by weight per 100 parts of iron. The amount of vermiculate can be varied greatly. Variation of any or all ingredients in quantity, particle size or grade will affect the rate of reaction and, thus, the temperatures achieved and the duration of the reaction.

The air- and moisture-permeable bag 12, instead of the preferred polyester material mentioned above, can be made of other synthetic fiber cloths or of natural materials such as cotton. The air and moisture-impermeable layer can be polyethylene, as noted above, or can be a wide variety of other materials, such as polypropylene or nylon film. Polyethylene is preferred for its heat-sealing ease.

Laminates may be in many different forms. The laminate as described above represents a highly preferred improvement. It provides an excellent tactile quality to the body-contact surfaces. And, we have discovered that the laminates as described contains the chemical mixture very well even though the perforations extend entirely through them.

Other acceptable materials for laminates include a suitable non-woven or woven material with a film layer, such as polyethylene, polypropylene, polyvinylidene chloride, or the like, or a metal foil or a metalized cloth which is impermeable except for its discrete perforations. Acceptable laminates will be well-known to one skilled in the art who are familiar with this invention.

Perforations can be made in many different ways, including cutting and punching. It has been found that the holes can be made of superior uniform size by the use of laser beams to burn or form the holes. In some cases it can be preferable to arrange the holes in a thin area or strip of the air- and moisture-impermeable layer as opposed to having the holes distributed throughout the layer. By having the holes arranged in a strip, it is possible to create a greenhouse effect which can provide for a conservation of the moisture within the chemical mixture, increasing the life of the chemical mixture. Acceptable modifications are within the ability of those skilled in the art who are familiar with this invention.

While the principles of this invention have been described in connection with specific embodiments, it should be understood clearly that these descriptions are made only by way of example and are not intended to limit the scope of the invention.

What is claimed:

1. In a heating pad of the type having a particulate chemical mixture which is exothermically reactive in the presence of air and having first and second opposed panels forming an envelope which contains the mixture while admitting air, the improvement comprising:

the first panel having a first body-contact surface and a first set of air-admitting perforations extending from the first body-contact surface to inside the envelope;

the second panel having a second body-contact surface and a second set of air-admitting perforations extending from the second body-contact surface to inside the envelope; and the second set of perforations differing structurally from the first set of perforations thereby to provide different air-admission properties supporting differing reaction characteristics, whereby two different heat conditions may be applied to the human body by the two body-contact surfaces with the opposite body-contact surfaces exposed to the atmosphere.

2. The heating pad of claim 1 wherein each of the panels, except for the perforations, comprises a substantially air- and moisture-impermeable material.

3. The heating pad of claim 2 wherein the at least one of the panels comprises a laminate, including at least one layer of the air- and moisture-impermeable material.

4. The heating pad of claim 3 wherein the laminate includes a layer of air- and moisture-permeable material.

5. The heating pad of claim 4 wherein the air- and moisture-permeable material is an outer layer to form one of the body-contact surfaces, whereby such body-contact surface has a good tactile quality.

6. The heating pad of claim 1 wherein the chemical mixture comprises a moist particulate mixture comprising carbon powder, iron powder, vermiculite, and a salt-water solution selected and in amounts to provide an exothermic reaction in air.

7. The heating pad of claim 1 wherein the chemical mixture, the first and second panels, and the perforation sets are selected to provide temperatures within a range of about 57.5-65 degrees C. at the first body-contact surface and within a range of about 50-57.5 degrees C. at the second body-contact surface.

8. The heating pad of claim 1 wherein the first and second panels differ in thickness, thereby contributing to the different heat conditions.

9. The heating pad of claim 8 wherein each of the panels, except for the perforations, comprises a substantially air- and moisture-impermeable material.

10. The heating pad of claim 9 wherein the at least one of the panels comprises a laminate, including at least one layer of the air- and moisture-impermeable material.

11. The heating pad of claim 10 wherein the laminate include a layer of air- and moisture-permeable material.

12. The heating pad of claim 1 wherein the perforations of the first set are of greater size than the perforations of the second set, allowing greater air flow through the first panel than through the second panel, thereby contributing to the different heat conditions.

13. The heating pad of claim 12 wherein each of the panels, except for the perforations, comprises a substantially air- and moisture-impermeable material.

14. The heating pad of claim 13 wherein the at least one of the panels comprises a laminate, including at least one layer of the air- and moisture-impermeable material.

15. The heating pad of claim 14 wherein the laminate includes a layer of air- and moisture-permeable material.

16. The heating pad of claim 1 wherein the first set of perforations has a greater number of perforations than the second set of perforations, allowing better access of air to the chemical mixture, thereby contributing to the different heat conditions.

17. The heating pad of claim 16 wherein each of the panels, except for the perforations, comprises a substantially air- and moisture-impermeable material.

18. The heating pad of claim 17 wherein the at least one of the panels comprises a laminate, including at least one layer of the air- and moisture-impermeable material.

19. The heating pad of claim 18 wherein the laminate includes a layer of air- and moisture-permeable material.

* * * * *